(12) United States Patent
Kondo et al.

(10) Patent No.: US 8,945,533 B2
(45) Date of Patent: Feb. 3, 2015

(54) ORAL CAVITY COMPOSITION

(75) Inventors: Keiichiro Kondo, Sagamihara (JP); Misao Yasumuro, Sagamihara (JP); Seigo Nakaya, Chuo-ku (JP); Nobuyuki Suzuki, Chuo-ku (JP)

(73) Assignees: Nippon Zettoc Co., Ltd., Chiyoda-Ku, Tokyo (JP); Wakamoto Pharmaceutical Co., Ltd., Chuo-Ku, Tokyo (JP)

( * ) Notice: Subject to any disclaimer, the term of this patent is extended or adjusted under 35 U.S.C. 154(b) by 1224 days.

(21) Appl. No.: 12/084,696

(22) PCT Filed: Nov. 14, 2006

(86) PCT No.: PCT/JP2006/322623
§ 371 (c)(1),
(2), (4) Date: May 8, 2008

(87) PCT Pub. No.: WO2007/055372
PCT Pub. Date: May 18, 2007

(65) Prior Publication Data
US 2009/0169492 A1    Jul. 2, 2009

(30) Foreign Application Priority Data

Nov. 14, 2005  (JP) ................. 2005-328659

(51) Int. Cl.
A61K 8/00    (2006.01)
A61K 8/02    (2006.01)
A61K 8/18    (2006.01)
A01N 63/00   (2006.01)
C12N 1/20    (2006.01)
A61Q 11/00   (2006.01)
A61K 8/99    (2006.01)

(52) U.S. Cl.
CPC . A61Q 11/00 (2013.01); A61K 8/99 (2013.01); Y10S 435/885 (2013.01)
USPC ............ 424/93.44; 424/49; 424/50; 424/401; 435/253.4; 435/885

(58) Field of Classification Search
CPC ............ A61K 2300/00; A61K 31/145; A61K 9/0014; A61K 31/165; A61K 31/704; A61K 47/10; A61K 47/14; A61K 47/32; A61K 47/38; A61K 9/0017; A61K 9/0046; A61K 9/0048; A61K 31/496; A61K 31/7036; A61K 38/08; A61K 8/97; A61K 2039/541
See application file for complete search history.

(56) References Cited

U.S. PATENT DOCUMENTS 2,944,941 A    7/1960  Goldenberg

FOREIGN PATENT DOCUMENTS

| | | |
|---|---|---|
| CN | 1114217 A | 1/1996 |
| JP | 2002-193777 A | 7/2002 |
| JP | 2002-234825 A | 8/2002 |
| JP | 2003-171292 A | 6/2003 |
| JP | 2004-250374 A | 9/2004 |
| JP | 2006-117601 A | 5/2006 |
| WO | WO 02/45726 A1 | 6/2002 |

OTHER PUBLICATIONS

Food and Development, vol. 38, No. 4, Apr. 2003, pp. 1-2.*
Internal Memorandum of Wakamoto Pharmaceutical Co., Ltd., dated Aug. 10, 2000, English translation.*
PCT/ISA/210.
PCT/ISA/237.
Masahiro Kawata et al., "Effects of lactic acid bacteria in biofilm formation of *Streptococcus mutans*", Bacterial Adherence & Biofilm, 2003, pp. 6-11, vol. 17.

* cited by examiner

*Primary Examiner* — Debbie K Ware
(74) *Attorney, Agent, or Firm* — Buchanan, Ingersoll & Rooney PC

(57) ABSTRACT

The object of the present invention is to provide an oral cavity composition which is nontoxic, excellent in plaque control, can prevent or treat onset of caries and periodontal disease caused by oral pathogens as well as can prevent or eliminate bad breath. The invention provides an oral cavity composition containing a lactic acid bacterium, *Streptococcus faecalis* as an active ingredient, the oral cavity composition wherein the lactic acid bacterium, *Streptococcus faecalis* is *Streptococcus faecalis* WB2000 strain and the oral cavity composition which is a non-aqueous oral cavity composition.

6 Claims, 3 Drawing Sheets

ORAL CAVITY COMPOSITION

This application is a national stage filing under 35 U.S.C. §371 of International Patent Application No. PCT/JP2006/322623, filed on Nov. 14, 2006, which claims the benefit of Japanese Patent Application No. 2005-328659, filed on Nov. 14, 2005.

TECHNICAL FIELD

The present invention relates to an oral cavity composition containing a lactic acid bacterium, *Streptococcus faecalis* as an active ingredient.

BACKGROUND ART

As a cause of dental caries and periodontitis, adherence of the plaque (dental plaque) is known, and it has been pointed out so far that its removal and prevention of the adherence, namely plaque control is important in oral hygiene. Mechanism of the plaque formation is as follows; glucosyltransferase which is an extracellular enzyme of an intraoral microorganism, particularly, *Streptococcus mutans* synthesizes sticky and insoluble glucan, using sucrose as the substrate and the glucan attaches to tooth plane to form plaque which is bacterial aggregate.

As methods of plaque control, mechanical plaque removal with the toothbrush etc. and intraoral bactericide with bactericidal agents are general. However, the mechanical methods by such as toothbrush cannot remove the plaque fully unless performed for long time with skilled brushing technique requiring training.

On the other hand, bactericidal effect by bactericidal agents also has limitation. There is a problem that the effect cannot be exerted fully to the bacterial aggregate, because the bactericidal agent does not penetrate to its inside. Therefore, devising is required such as increasing of concentration of bactericides and making the processing time longer. Additionally, plaque removal by bactericides was not always satisfactory in terms of safety, economy and efficacy since they effect on all bacteria in the oral cavity resulting in killing bacteria oral indigenous and bacteria useful to human body.

Dentifrices and the like combining lactic acid bacteria or fermentation liquid of lactic acid bacteria have been proposed as oral cavity compositions containing bactericidal ingredients gentle to the human body, for example, in JP 2002-234825A and JP 2002-193777A. This condition can be explained as follows: when the dentifrices and the like effect in the oral cavity where offending bacteria of dental caries and periodontal disease exist, the offending bacteria of dental caries and periodontal disease fall into bacteriostasis that is caused by struggle for survival between bacteria each other. However, it has not always been satisfactory.

In view of conventional arts for plaque control using lactic acid bacteria as described above, there has been a demand for development of oral cavity preparations combining lactic acid bacteria which have properties such as inhibiting plaque formation by inhibiting *Streptococcus mutans* effectively which is a major cause of plaque formation as well as ability of inhibiting generation of bad breath.

SUMMARY OF THE INVENTION

An object of the present invention is to provide an oral cavity composition which is nontoxic, excellent in plaque control, can prevent or treat onset of dental caries and periodontal disease caused by oral pathogens as well as can prevent or eliminate bad breath.

The present inventors, after intensive studies and search for various lactic acid bacteria to achieve the above object, have found *Streptococcus faecalls* excellent inhibitory effect on plaque formation, and useful for treatment and prevention of periodontal disease and bad breath, thereby leading to completion of the present invention invention.

Thus, the present invention is an oral cavity composition containing a lactic acid bacterium, *Streptococcus faecalis* as an active ingredient.

As a preferred aspect of the oral cavity composition of the present invention, there is a non-aqueous oral cavity composition.

A lactic acid bacterium, *Streptococcus faecalis* can inhibit offending bacteria of periodontal disease/dental caries such as *Streptococcus mutans* and perform plaque control, while it can normalize oral flora without disrupting it. Accordingly, *Streptococcus faecalis* exerts inhibitory effect on plaque formation, is useful for prevention of onset of periodontal disease or treatment of periodontal disease, and is further useful for prevention of bad breath generation or elimination of bad breath.

The oral cavity composition of the present invention exerts inhibitory effect on plaque formation and can be used in plaque control, while normalizing oral flora. The oral cavity composition of the present invention can also be used for prevention of onset of periodontal disease or treatment of periodontal disease, and prevention or elimination of bad breath. Periodontal diseases herein include gingivitis and periodontitis.

BEST MODE FOR CARRYING OUT THE INVENTION

Figure 1:
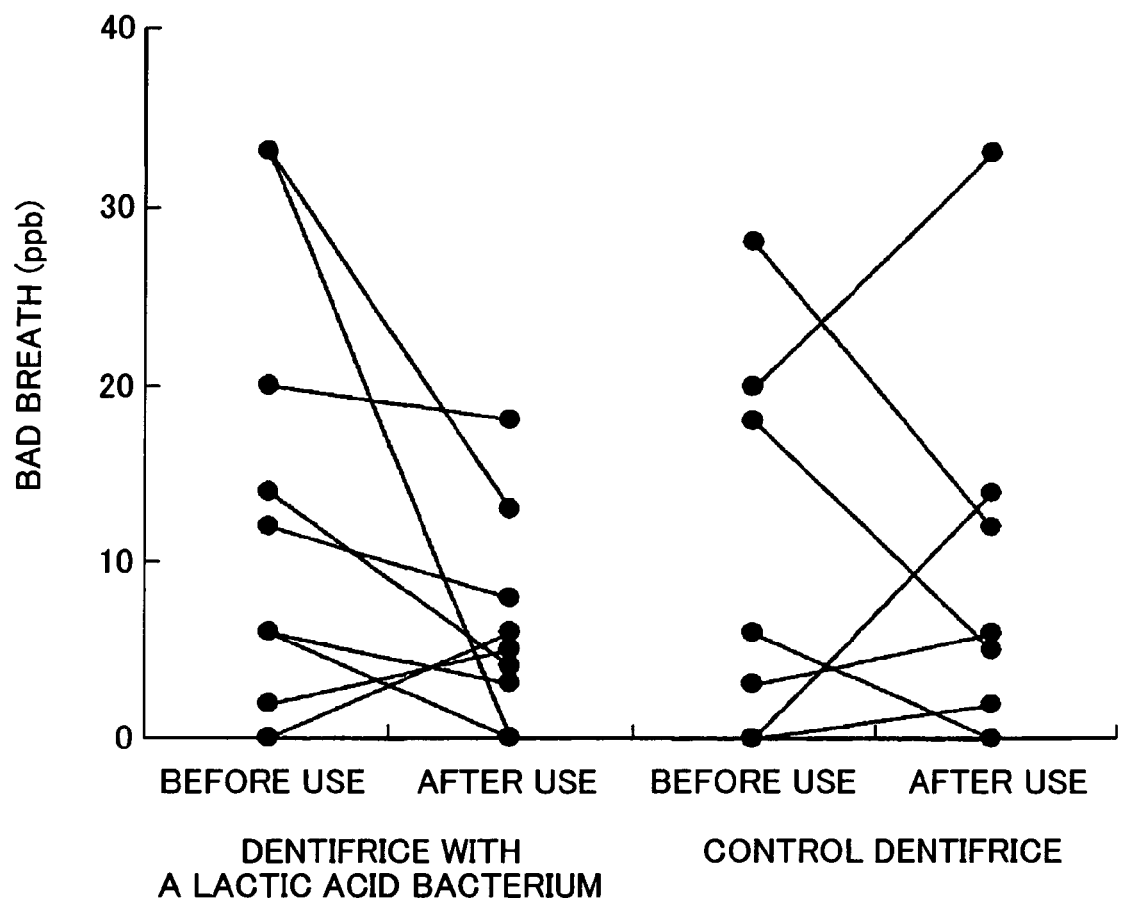
FIG. 1 is a graph representing the results of the bad breath of each subject measured in Test Example 2.

The oral cavity composition of the invention can be provided in different forms including dentifrices such as toothpastes, liquid (gel) dentifrices and moist dentifrices, creams, ointments, mouth refrigerants, mouth-wash, patches, films, chewing gums and gargles.

A lactic acid bacterium, *Streptococcus faecalis* used in the present invention is the one which is referred to as *Enterococcus faecium* in the current classification. A lactic acid bacterium, *Streptococcus faecalis* used in the present invention may be in any form, for example, freeze-dried product in powder form.

Appropriately, the content of a lactic acid bacterium, *Streptococcus faecalis* in the oral cavity composition of the present invention is in a range of 0.001 to 20% by weight, preferably, 0.01 to 10% by weight, more preferably, 0.1 to 5% by weight relative to the total weight of the oral cavity composition.

The oral cavity composition of the present invention can combine the following ingredients in appropriate amounts as needed according to its form in addition to the above active ingredients.

The polishing agent includes silica polishing agent such as silica gel, precipitating silica, pyrogenetic silica, hydrous sicic acid, silicic acid anhydride, zeolite, aluminosilicate, zirconosilicate and the like, crystalline cellulose, calcium hydrogen phosphate dihydrate, calcium hydrogen phosphate anhydride, calcium pyrophosphate, trimagnecium phosphate, tricalcium phosphate, aluminum hydroxide, alumina, light calcium carbonate, heavy calcium carbonate, magnesium carbonate, zirconium silicate, synthetic resin polishing agents and the like. One or more of them can be used in combination. The amount of the polishing agent is generally in the range of 0 to 60% by weight, preferably, 10 to 45% by weight relative to the total amount of the oral cavity composition.

The wetting agent includes polyalcohols such as glycerin, concentrated glycerin, diglycerin, sorbitol, multitol, dipropylene glycol, propylene glycol, 1,3-butylene glycol, xylitol, polyethylene glycol and the like, and one or more of them can be used.

The binder includes carrageenan (τ, λ, κ), alginic acid and its derivatives such as alginate, sodium alginate, propylene glycol alginate ester, sodium alginate containing calcium, potassium alginate, calcium alginate, ammonium alginate and the like, xanthan gum, guar gum, gelatin, agar, sodium carboxymethylcellulose, hydroxyethylcellulose, hydroxypropylcellulose, sodium polyacrylate and the like, and one or more of them can be used.

The foaming agent includes sodium laurylsulfate, sodium lauroylsarcosine, sodium alkylsulfosuccinate, sodium sulfonate monoglycerin coconut oil fatty acid, sodium alpha olefin sulfonate and N-acylaminoadd salts such as N-acylglutamate, 2-alkyl-N-carboxymethyl-N-hydroxyethylimidazoliniumbetaine, multitol fatty add esters, sucrose fatty acid esters, glycerin fatty acid esters, polyglycerin fatty add esters, fatty acid diethanol amide, polyoxyethylene sorbitan monostearate, polyoxyethylene hydrogenated castor oil, polyoxyethylene fatty add esters and the like, and one or more of them can be used.

The sweetener includes saccharin sodium, aspartame, trehalose, stevioside, stevia extract, paramethoxy cinnamic aldehyde, neohesperidildihydrochalcone, perillartin and the like.

The preservative includes parabens such as methylparaben, ethylparaben, propylparaben, butylparaben and the like, sodium benzoic acid, phenoxyethanol, alkyldiaminoethylglycin hydrochloride and the like.

As the flavor ingredient, one or more of the following can be used in combination: 1-menthol, anethole, menthone, cineol, limonene, carvone, methylsalicylate, ethylbutyrate, eugenol, thymol, cinnamic aldehyde, trans-2-hexenal and the like. These ingredients may be combined singly, or essential oils and the like containing these may be used.

In addition to the above flavor ingredients, the flavor ingredients including fatty alcohols and their esters, terpene hydrocarbons, phenol ethers, aldehydes, ketones, lactones and the like or essential oils may be combined within the range where the effect of the invention is not interfered. The combination amount of the above flavors is generally in the range of 0.02 to 2% by weight relative to the total amount of the oral cavity composition.

Additional active ingredients besides those described above may be combined in the oral cavity composition of the invention. Such active ingredient includes lysozyme chloride, sodium fluoride, potassium fluoride, sodium monofluorophosphate, polyethyleneglycol, polyvinylpyrolidone, hinokitiol, ascorbic acid, ascorbic acid salts, chlorhexidine salts, cetylpyridinium chloride, benzalkonium chloride, benzethonium chloride, bisabolol, tricrosan, isopropylmethylphenol, tocopherolacetate, ϵ-aminocaproic acid, tranexamic acid, aluminumhydroxylahantoin, aluminum lactate, dihydrocholesterol, glycyrrhetinic acid, glycyrrhizic acid salts, copper chlorophyllin salts, sodium chloride, guaiazulenesulfonic add salts, dextranase, pyridoxine hydrochloride, medicinal hydroxyapatite and the like, and one or more of them can be combined.

The oral cavity composition of the present invention can be prepared according to the conventional methods, and the preparing methods are not particularly limited.

The oral cavity composition of the present invention can be filled in such as aluminum tubes, laminate tubes, glass deposition tubes, plastic tubes, plastic bottles, aerosol containers and the like.

A non-aqueous oral cavity composition is also a preferred aspect of the oral cavity composition of the invention. The non-aqueous oral cavity composition herein means the oral cavity composition which contains no water or almost no water, particularly, the one in which the content of water is 0 to 3% by weight, preferably 0 to 1% by weight, more preferably in which there is no content of water, relative to the total amount of the oral cavity composition.

The present invention will be described in detail in the following test examples and examples, but the invention is not limited to such description.

In addition, as a lactic add bacterium, *Streptococcus faecalis*, *Streptococcus faecalis* WB2000 strain made by Wakamoto Pharmaceutical Co., Ltd. was used in the following test examples and examples. *Streptococcus faecalis* VWB2000 strain is widely and commonly used in pharmaceuticals and food and can be purchased from Wakamoto Pharmaceutical Co., Ltd.

Test Example 1

Inhibition test of dental plaque formation by various lactic acid bacteria
<Test Method>

A dental plaque forming bacterium, *Streptococcus mutans* and various lactic acid bacteria (*Bifidobacterum longum, Bifidobactrium bifidum, Lactobacillus acdophilus, Streptococcus faecalis*) were cocultured, and it was evaluated whether various lactic acid bacteria inhibit the dental plaque formed by *S. mutans*. Culture of *Streptococcus mutans* was tested as a control similarly.

Namely, 0.1 ml of bacterial suspension obtained after culturing *S. mutans* in the SCD liquid medium at 37° C. for 24 hr and 0.1 ml of bacterial suspension obtained after culturing various test lactic acid bacteria in the SCD liquid medium at 37° C. for 24 hr were added to 4.8 ml of BHI liquid medium supplemented by 5% sucrose, mixed in a test tube to make 5 ml of reaction liquid. The reaction liquid was allowed to stand at 30° of elevation angle, reacted at 37° C. for 24 hr under anaerobic condition. The insoluble glucan formed in the reaction liquid was assigned as a non-adhering fraction by decanting the reaction liquid to another test tube. Further, the adhering fraction was washed with 5 ml of purified water, and the detached insoluble glucan was added to the said test tube as the non-adhering fraction. This was performed twice and the insoluble glucan left on the wall of the test tube was assigned as adhering fraction. The amount of insoluble glucan was dissolved with 5 ml of 1N NaOH, measured by phenol sulphate method, and the combined amount of the non-adhering and adhering fractions was assigned as the total amount of glucan. Further, difference between the total amount of glucan of the control reaction liquid and the total amount of glucan of the coculture reaction liquid was obtained, and an inhibition rate of plaque formation of each coculture reaction liquid was calculated from the difference.

The result is shown in the following table.

TABLE 1

|  | Total Amount of Glucan (mg/ml) | Inhibition Rate (%) of Dental Plaque Formation |
|---|---|---|
| S. mutans only (control) | 5495 | — |
| S. mutans + B. longum | 1536 | 72.0 |
| S. mutans + B. bifidum | 1262 | 77.0 |
| S. mutans + L. acidophilus | 1875 | 65.9 |
| S. mutans + S. faecalis | 1031 | 81.2 |

Test Example 2

Use test using dentifrices combined with a lactic acid bacterium, *Streptococcus faecalis*.

<Test Method>

Ten test subjects were divided into two groups (group A and group B). Subjects in group A were made to brush their teeth with the dentifrice combined with a lactic acid bacterium, *Streptococcus faecalis* (for composition, see Example 1 in Table 2) twice a day, in the morning and in the evening, and subjects in group B were made to brush their teeth with the control dentifrice (for composition, see Comparative Example 1 in Table 2) similarly. The dentifrice used in both groups was a toothpaste.

TABLE 2

| Ingredient (% by weight) | Example 1 | Comparative Example 1 |
|---|---|---|
| Calcium hydrogen phosphate | 32.0 | 32.0 |
| Polyethylene glycol | 10.0 | 10.0 |
| 1,3-butylene glycol | 43.2 | 43.3 |
| Hydroxypropylcellulose | 1.0 | 1.0 |
| Silicic acid anhydride | 6.0 | 6.0 |
| Xylitol | 1.0 | 1.0 |
| Glycerin fatty acid ester | 2.0 | 2.0 |
| *Streptococcus faecalis* | 0.1 | — |
| Saccharin sodium | 0.5 | 0.5 |
| Sodium benzoate | 0.5 | 0.5 |
| Vitamin E | 0.1 | 0.1 |
| Glycyrrhetinic acid | 0.1 | 0.1 |
| Ethanol | 2.0 | 2.0 |
| Menthol | 0.6 | 0.6 |
| Flavor | 0.9 | 0.9 |
| Total | 100.0 | 100.0 |

Tooth brushing period was set as 2 weeks, saliva was collected and bad breath was measured every other week. Further, the dentifrices of the group A and group B were exchanged and tested similarly which was set as the cross over test. Total number of streptococci and the number of *S. mutans* were detected from the collected saliva using the culturing method, and the rate of dental carious bacteria ((the number of *S. mutans*/total number of streptococci)×100(%)) was calculated from the rate of *S. mutans* to the total streptococci. Halimeter (made by Interscan Corp.) was used for measurement of bad breath.

Figure 2:
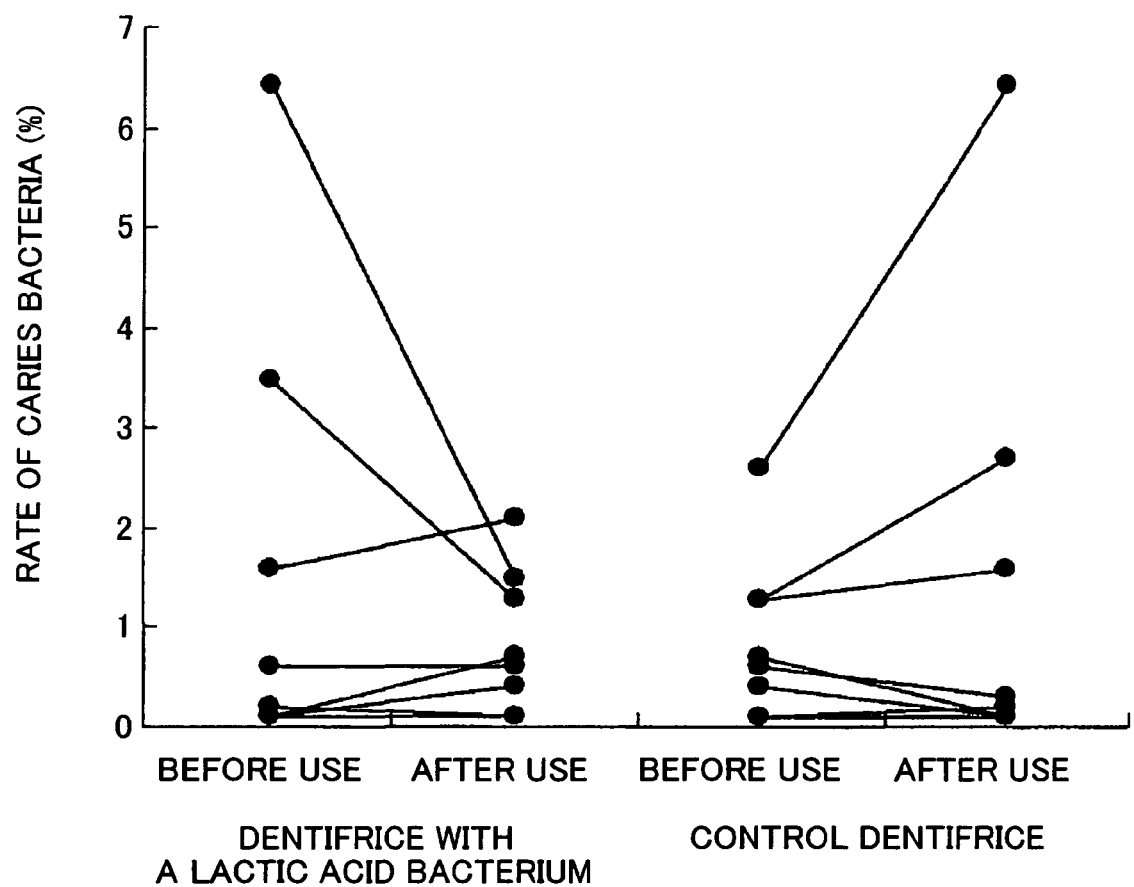
FIG. 2 is a graph representing the rate of caries bacteria of each subject calculated in Test Example 2.
Figure 3:
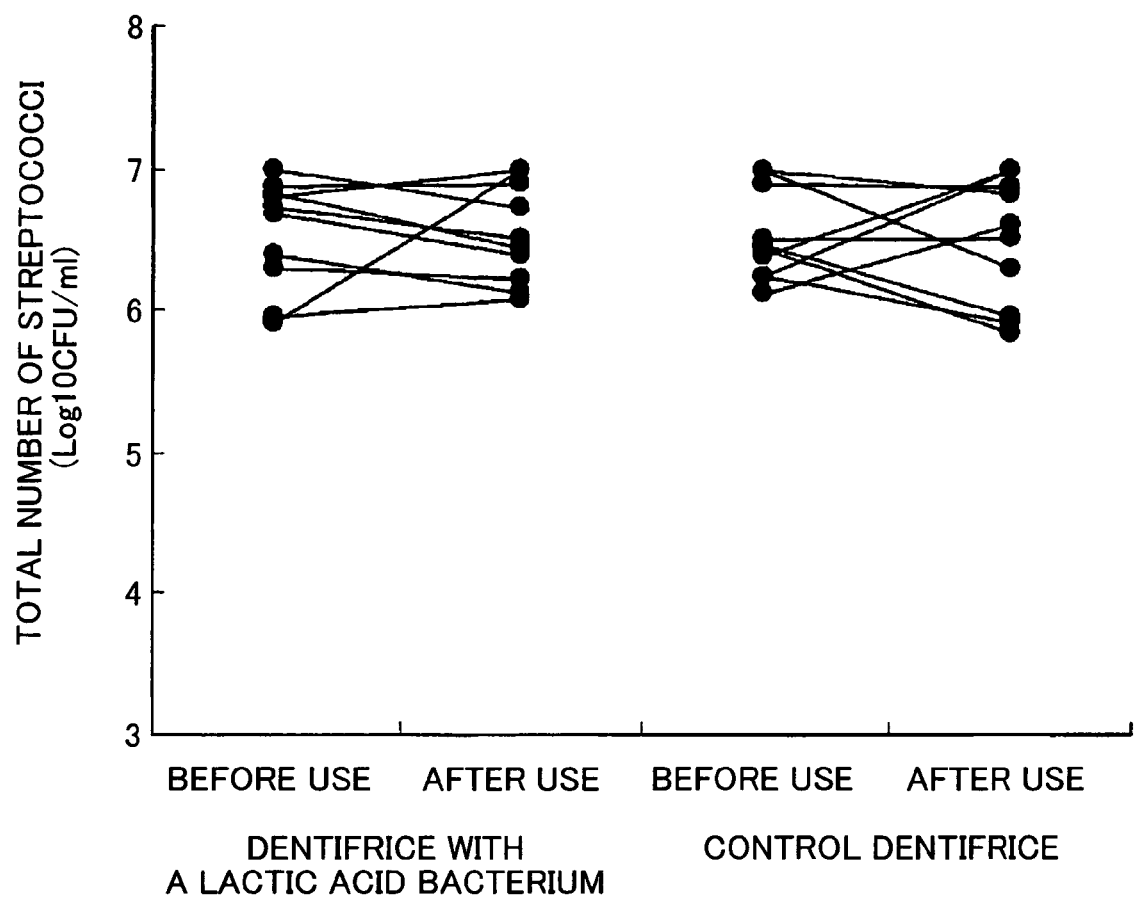
FIG. 3 is a graph representing the total number of streptococci of each subject detected in Test Example 2.

The results were shown in FIG. 1 for the bad breath, in FIG. 2 for the rate of dental carious bacteria, and in FIG. 3 for total number of streptococci.

Further, evaluation of those results is as follows.

TABLE 3

| Evaluation Items | Use of dentifrices combined with a lactic acid bacterium | Use of Control Dentifrices |
|---|---|---|
| Total *streptococci* | unchanged | unchanged |
| Rate of carious bacteria | inclined to decrease | unchanged |
| Bad breath | inclined to decrease | unchanged |

Although there was no significant difference observed for the rate of dental carious bacteria, it was noticed that the test subjects who had high rate of carious bacteria was inclined to decrease the rate by using the dentifrices combined with a lactic acid bacterium.

It was noticed that bad breath was inclined to be improved by use of the dentifrices combined with a lactic acid bacterium, though there was no significant difference.

Change in the total number of streptococci was not noticed by use of the dentifrices combined with a lactic acid bacterium. It was considered that there is no major change in the bacterial flora of the oral cavity by use of the dentifrices combined with a lactic acid bacterium.

From the above results, improvement of bad breath, reduction of risk of caries and reduction of risk of periodontal disease were expected by use of the dentifrices combined with a lactic acid bacterium.

Further, following toothpastes were prepared.

Example 2

Preparation of Dental Paste

| | |
|---|---|
| Hydroxypropylcellulose | 3.0% by weight |
| Polyethylene glycol | 48.65 |
| Crystalline cellulose | 10.0 |
| Aluminum hydroxide | 35.0 |
| *Streptococcus faecalis* WB2000 | 1.0 |
| Sodium laurylsulfate | 1.0 |
| Saccharin sodium | 0.1 |
| Paraben | 0.1 |
| Flavor | 1.0 |
| Tocopheryl acetate | 0.1 |
| Cetylpyridinium chloride | 0.05 |
| Total | 100.0% by weight |

Example 3

Preparation of Dental Paste

| | |
|---|---|
| Hydroxypropylcellulose | 1.0% by weight |
| Diglycerine | 22.0 |
| Propylene glycol | 23.17 |
| Silicic acid anhydride | 5.0 |
| Crystalline cellulose | 10.0 |
| *Streptococcus faecalis* WB2000 | 1.0 |
| Sodium fluoride | 0.2 |
| Calcium carbonate | 35.0 |
| Sodium laurylsulfate | 1.0 |
| Sodium lauroylsarcosin | 0.3 |
| *Stevia* extract | 0.1 |
| Sodium benzoate | 0.1 |
| Flavor | 1.0 |

| | |
|---|---|
| Dipotassium glycyrrhizinate | 0.1 |
| Isopropylmethylphenol | 0.03 |
| Total | 100.0% by weight |

Example 4

Preparation of Dental Paste

| | |
|---|---|
| Hydroxypropylcellulose | 10.0% by weight |
| Concentrated glycerin | 19.0 |
| Polyethylene glycol | 10.0 |
| 1,3-butylene glycol | 10.8 |
| Silicic acid anhydride | 10.0 |
| *Streptococcus faecalis* WB2000 | 0.1 |
| ε-aminocaproic acid | 0.1 |
| Calcium hydrogen phosphate for dentifrices | 25.0 |
| Sucrose fatty acid ester | 0.5 |
| Xylitol | 10.0 |
| Carrageenan | 0.3 |
| Paraben | 0.1 |
| Flavor | 1.0 |
| Purified water | 3.0 |
| β-glycyrrhetinic acid | 0.05 |
| Chlorhexidine hydrochloride | 0.05 |
| Total | 100.0% by weight |

Example 5

Preparation of Dental Paste

| | |
|---|---|
| Hydroxypropylcellulose | 3.0% by weight |
| Concentrated glycerin | 54.95 |
| Silicic acid anhydride | 20.0 |
| Hydrous silicic acid | 10.0 |
| Crystalline cellulose | 8.0 |
| Lysozyme chloride | 0.3 |
| Sodium laurylsulfate | 1.0 |
| Sodium lauroylsarcosin | 0.3 |
| *Streptococcus faecalis* WB2000 | 0.3 |
| Paraben | 0.1 |
| Flavor | 1.0 |
| Zeolite | 1.0 |
| Cetylpyridinium chloride | 0.05 |
| Total | 100.0% by weight |

Example 6

Preparation of Dental Paste

| | |
|---|---|
| Ground calcium carbonate | 30.0% by weight |
| Concentrated glycerin | 15.0 |
| Sorbitol | 5.0 |
| Sodium carboxymethylcellulose | 1.0 |
| Silicic acid anhydride | 10.0 |
| *Streptococcus faecalis* WB2000 | 1.0 |
| Hinokitiol | 0.05 |
| ε-aminocaproic acid | 0.1 |
| Sodium laurylsulfate | 0.5 |
| Polyoxyethylene hydrogenated castor oil | 5.0 |
| Trehalose | 5.0 |
| Xylitol | 5.0 |
| Flavor | 1.0 |
| Sodium chloride | 10.0 |
| Purified water | q.s. |
| Total | 100.0% by weight |

Example 7

Preparation of Dental Paste

| | |
|---|---|
| Calcium phosphate for dentifrices | 30.0% by weight |
| Silicic acid anhydride | 5.0 |
| Concentrated glycerin | 15.0 |
| Sorbitol | 5.0 |
| Sodium carboxymethylcellulose | 1.0 |
| *Streptococcus faecalis* WB2000 | 0.5 |
| Cetylpyridinium chloride | 0.05 |
| Tocopheryl acetate | 0.1 |
| Sodium laurylsulfate | 0.5 |
| Polyoxyethylene hydrogenated castor oil | 5.0 |
| Xylitol | 5.0 |
| Flavor | 1.0 |
| Purified water | q.s. |
| Total | 100.0% by weight |

Example 8

Preparation of Dental Paste

| | |
|---|---|
| Cacium pyrophosphate | 30.0% by weight |
| Silicic acid anhydride | 5.0 |
| Concentrated glycerin | 15.0 |
| Carrageenan | 0.5 |
| Sodium carboxymethylcellulose | 0.8 |
| *Streptococcus faecalis* WB2000 | 0.5 |
| Cetylpyridinium chloride | 0.05 |
| *Stevia* extract | 0 1 |
| Sodium laurylsulfate | 0.5 |
| Polyoxyethylene hydrogenated castor oil | 5.0 |
| Flavor | 1.0 |
| Purified water | q.s. |
| Total | 100.0% by weight |

Example 9

Preparation of Dental Paste

| | |
|---|---|
| Silicic acid anhydride | 10.0% by weight |
| Concentrated glycerin | 15.0 |
| Sorbitol | 5.0 |
| Carrageenan | 1.0 |
| *Streptococcus faecalis* WB2000 | 0.5 |
| Cetylpyridinium chloride | 0.05 |
| Sodium benzoate | 0.1 |
| Sodium laurylsulfate | 0.5 |
| Xylitol | 5.0 |
| Flavor | 1.0 |
| Purified water | q.s. |
| Total | 100.0% by weight |

What is claimed is:

1. An oral cavity composition containing as a bacterium, solely *Streptococcus faecalis* WB2000.

2. The oral cavity composition according to claim 1, wherein the composition is a non-aqueous oral cavity composition.

3. The oral cavity composition according to claim 1, wherein the composition is a dentifrice.

4. A process for inhibiting plaque formation in a human comprising regularly applying an oral cavity composition containing as a bacterium, solely *Streptococcus faecalis* WB2000.

5. The process according to claim 4, wherein the oral cavity composition is a non-aqueous oral cavity composition.

6. The process according to claim 4, wherein the oral cavity composition is a dentifrice.

* * * * *